United States Patent [19]

Lalezari et al.

[11] Patent Number: 5,093,367
[45] Date of Patent: Mar. 3, 1992

[54] METHOD OF SYNTHESIS AND NOVEL COMPOUNDS FOR PHARMACEUTICAL USES

[75] Inventors: Iraj Lalezari; Parviz Lalezari, both of Scarsdale, N.Y.

[73] Assignee: Montefiore Medical Center, Bronx, N.Y.

[21] Appl. No.: 477,048

[22] Filed: Feb. 7, 1990

Related U.S. Application Data

[62] Division of Ser. No. 207,098, Jun. 15, 1988, Pat. No. 4,921,997.

[51] Int. Cl.⁵ ............................................ A61K 31/195
[52] U.S. Cl. .................................... 514/564; 514/539; 560/34; 562/439
[58] Field of Search .......................... 562/439; 560/34; 514/564, 539

[56] References Cited

FOREIGN PATENT DOCUMENTS 2614045 1/1976 Fed. Rep. of Germany .
1055619 1/1967 United Kingdom ................ 562/439

*Primary Examiner*—Bruce Gray
*Attorney, Agent, or Firm*—Hedman, Gibson & Costigan

[57] ABSTRACT

The present invention is concerned with a process for the synthesis of substituted arylureidophenexymethyl propionic acids and an analogous benzamides series of compounds which have activity in the dissociation of oxygen from hemoglobin. In addition the process may be utilized to prepare compounds which are known.

8 Claims, No Drawings

METHOD OF SYNTHESIS AND NOVEL COMPOUNDS FOR PHARMACEUTICAL USES

This is a divisional application of U.S. patent application Ser. No. 07/207,098, filed June 15. 1988 now U.S. Pat. No. 4,921,997.

BACKGROUND OF THE INVENTION

The present invention is concerned with a process for the synthesis of novel substituted arylureidophenoxymethylpropionic acids and an analogous benzamido series of compounds which have exceptional activity in the, dissociation of oxygen from hemoglobin. In addition the novel process may be utilized to prepare compounds which are known.

Accordingly, it is a primary object of this invention to provide an improved method for the synthesis of arylureidophenoxymethylpropionic acids.

It is also an object of this invention to provide novel arylureidophenoxymethyl propionic acids.

These and other objects will become apparent from the present specification.

SUMMARY OF THE INVENTION

The present invention is concerned with a novel process for the preparation of compounds of the formula:

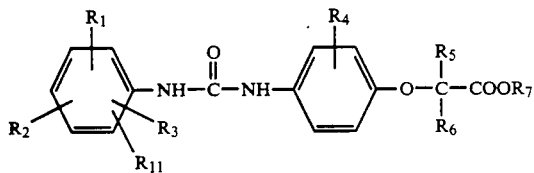

wherein $R_1$, $R_2$, $R_3$, $R_4$ and $R_{11}$ may be the same or different and are independently selected from the group consisting of hydrogen, halogen, straight or branched chain alkyl of from 1-6 carbon atoms, aryl, cycloalkyl of 3 to 7 carbon atoms; and alkoxy of 1 to 6 carbon atoms; $R_5$ and $R_6$ may be the same or different and are selected from the group consisting of hydrogen, halogen, straight or branched chain alkyl groups of from 1 to 6 carbon atoms, aralkyl groups wherein the alkyl portion has from 1 to 6 carbon atoms, cycloalkyl of from 3 to 7 carbon atoms and aryl; $R_7$ is hydrogen or a straight or branched chain alkyl group of 1 to 6 carbon atoms and the pharmaceutically acceptable salts thereof such as the sodium, potassium, ammonium etc.

The invention is also concerned with novel compounds of the formula:

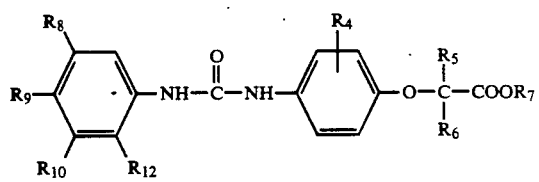

wherein $R_4$, $R_5$, $R_6$ and $R_7$ are the same as hereinabove described; $R_8$ is halogen; $R_9$ is halogen or hydrogen; $R_{10}$ is halogen or hydrogen; $R_{12}$ is hydrogen or halogen with the proviso that $R_9$ may only be hydrogen when $R_8$ and $R_{12}$ are halogen and the pharmaceutically acceptable salts thereof.

The invention also provides novel processes for the preparation of the following compounds:

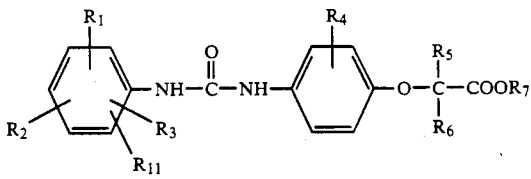

and

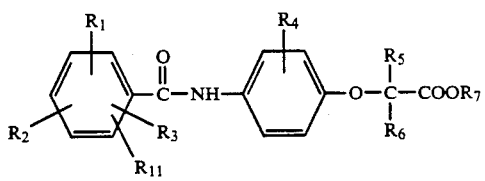

wherein $R_1$, $R_2$, $R_3$, $R_4$ and $R_{11}$ are the same as hereinabove described.

DETAILED DESCRIPTION OF THE INVENTION

The processes of the invention include a process for producing compounds of the formula:

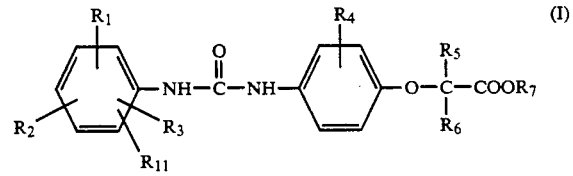

wherein $R_1$, $R_2$, $R_3$, $R_4$, $R_5$, $R_6$, $R_7$ and $R_{11}$ are as hereinabove described, which comprises contacting a compound of the formula:

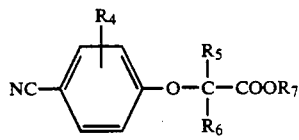

with a sufficient amount of a peroxide such as hydrogen peroxide in aqueous alkali hydroxide to form a carboxamide of the formula:

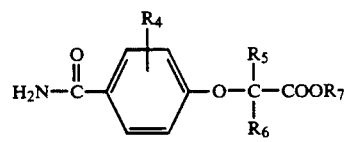

This compound is reacted with a hypobromite of the formula MOBr wherein M is sodium or potassium to give an amino compound of the formula:

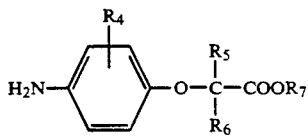

recovering said amino compound and contacting said amino compound with a compound of the formula:

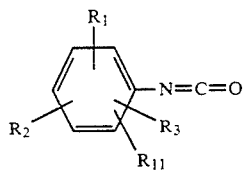

in the presence of dry pyridine to form a reaction product and thereafter recovering from said reaction product a compound of formula I.

The above described process may be utilized to prepare compounds of formula II.

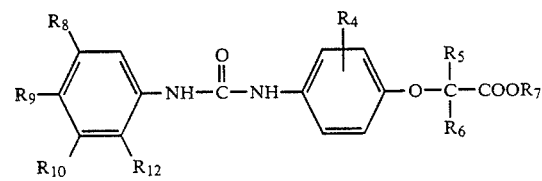

wherein $R_8$ is halogen; $R_9$ is halogen or hydrogen; $R_{10}$ is chloro; $R_{12}$ is hydrogen or halogen with the proviso that $R_9$ may only be hydrogen when $R_8$ and $R_{12}$ are halogen and the pharmaceutically acceptable salts thereof; $R_4$, $R_5$, $R_6$ and $R_7$ are the same as hereinabove described.

The invention also includes a process for the preparation of compounds of formula I, which is based on contacting a compound of the formula:

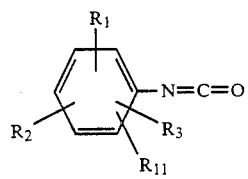

with a para amino phenol of the formula:

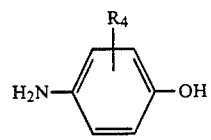

to form an intermediate compound of the formula:

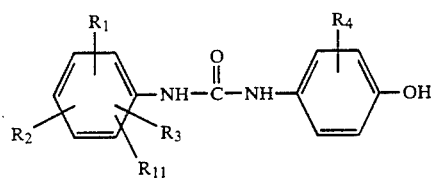

and thereafter contacting said intermediate compound with chloroform and a compound of the formula:

in the presence of anhydrous alkali to form a compound of formula I.

A further process within the scope of the present invention is concerned with the production of compounds of the formula:

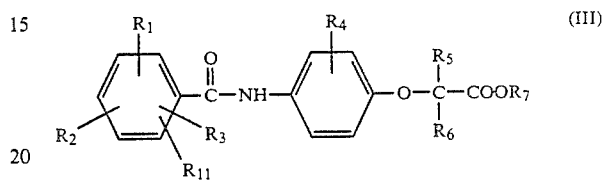

wherein $R_1$, $R_2$, $R_3$, $R_4$, $R_5$, $R_6$, $R_7$ and $R_{11}$ are the same as hereinabove defined. This process is based on the reaction of an amino phenol of the formula:

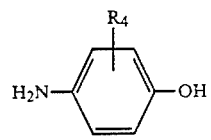

with ethyl chloroformate in the presence of alkali, eg. NaOH, KOH, LiOH to form a compound of the formula:

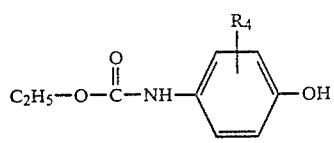

which is then reacted with anhydrous alkali such as dry pellets of sodium or potassium hydroxide, chlorofrom and a compound of the formula:

to form a compound of the formula:

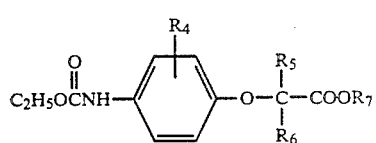

which is thereafter contacted with aqueous alkali to form the corresponding amino compound. The amino compound is contacted with a compound of the formula:

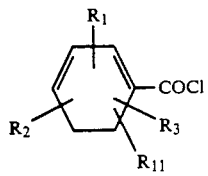

to form a compound of formula III or with an aryl isocyanate to give compounds of formula I. These processes provide exceptionally high yields of the compounds as compared to the yields obtained by other methods.

The compounds of formulas I, II and III may be administered to mammals including humans to reduce or prevent hyperlipidemia especially to reduce the levels of total serum cholesterol, low density lipoprotein-associated cholesterol and triglycerides. The compounds may be administered orally at a daily dosage of from about 1 to 200 mg per kilogram of body weight and more preferably at a level of about 10 to 100 mg and most preferably 1 to 50 mg per kilogram of body weight. The daily dosage is to be administered as a single dose, or in divided amounts three or four times a day. It is understood that the dose may be varied according to individual sensitivity and the type of hyperlipidemia being treated. In addition the compounds may be administered parenterally or rectally. The parenteral dose will be 15–25% of the oral dosage and the rectal dosage may be adjusted to obtain the desired therapeutic affect.

The compounds of the invention may be added to whole blood or packed cells in an amount of about 50 mg to 2.0 g per unit of blood (473 ml) or unit of packed cells (235 ml) and preferably from 250 mg to 750 mg per unit of blood or unit of packed cells in order to facilitate the dissociation of oxygen from hemoglobin and improve the oxygen delivery capability of blood. When blood is stored, the hemoglobin in the blood tends to increase its affinity for oxygen by losing 2,3-diphosphoglycerides. The compounds of the invention are capable of reversing and/or preventing the functional abnormality of hemoglobin which is observed when whole blood or packed cells are stored. The compounds of the invention may be added to whole blood or red blood cell fractions in a closed system using an appropriate resevoir in which the compound is placed in dry form or in a solution form prior to storage or which is present in the anticoagulating solution in the blood collecting bag.

It may be desirable to administer the compound to a patient prior to and/or simultaneously with the transfusion of the treated whole blood or red cells in order to avoid substantial variations in the hemoglobin oxygen affinity due to dilution that occurs when the blood is administered.

The compounds may be administered to patients in whom the affinity of hemoglobin for oxygen is abnormally high. Particular conditions include certain hemoglobinopathies and certain respiratory distress syndromes in newborn infants aggravated by high fetal hemoglobin levels and when the availability of hemoglobin to tissues is decreased (e.g. in ischemic conditions such as peripheral vascular disease, coronary occlusion or cerebral vascular accidents). The compounds may also be used to inhibit platelet aggregation and may be used for antithrombotic purposes. The dosage for the modification of the affinity of hemoglobin for oxygen may be based on the dosages set forth above for hyperlipidemia and these dosages may be adjusted for parenteral use to obtain the desired therapeutic result. The compounds should not be administered to patients with sickle cell disease to avoid the possibility of excessive oxygen loss which may precipitate a sickle cell crisis.

The compounds may also be administered at levels of 1 to 100 mg in a single dose per kilogram of body weight alone or combination with oxygen in conjunction with radiation therapy or with chemotherapy for malignant conditions such as solid tumors of the breast, stomach, colon and their metastatic lesions. The compounds should be administered sufficiently prior to the initiation of chemotherapy or radiation therapy so that the blood level of the compound will be at a maximum. This will increase the efficacy of the treatment and/or make it possible to reduce the radiation or drug dose and reduce the associated toxicites. The compounds may also be used at levels of 1–100 mg per Kg of body weight for treatment of CO poisoning to facilitate dissociation of hemoglobin-bound CO and its replacement with oxygen. Efficacy of this treatment will be increased if the compounds are administered simultaneously with oxygen.

As used herein the term halogen is used to include bromo, chloro, fluoro and iodo; the term alkyl includes straight and branched chain hydrocarbon groups of 1–6 carbon atoms such as methyl, ethyl, n-propyl, n-pentyl and the like; the term aryl includes phenyl and naphthyl; the term cycloalkyl includes cycloaliphatic groups of 3 to 7 carbon atoms such a cyclopropyl, cyclobutyl, cyclohexyl and the like; the term alkoxy is used to include $R_{13}OH$ groups wherein $R_{13}$ is alkyl of 1 to 6 carbon atoms; the term aralkyl is used to include phenalkyl groups wherein the alkyl portion is an alkylene moiety of 1–6 carbons such as benzyl, phenethyl, phenpropyl and the like. The meaning of $R_1$, $R_2$, $R_3$, $R_4$, $R_5$, $R_6$, $R_7$, $R_8$, $R_9$, $R_{10}$, $R_{11}$, $R_{12}$ and $R_{13}$ are the same for each formula except where specific meanings are set forth.

The term pharmaceutically acceptable diluent is used to include liquid and solid materials utilized to prepare injectable dosage forms and solid dosage forms such as tablets and capsules. Water may be used for the preparation of injectable compositions which may include buffers and agents to render the injectable composition isotonic. The solid diluents and excipients include lactose, starch, conventional disintegrating agents, coatings and the like. For example, UK patent no. 1,535,683, which is incorporated by reference, gives several embodiments of formulation that may be utilized in the preparation of tablets and capsules.

EXAMPLE 1

2-(4-cyanophenoxy)-2-methylpropionic acid

To a warm stirring mixture of 4-cyanophenol, 5.95 g (0.05 mole) and 11 g NaOH in 45 ml acetone, chloroform. 3.8 ml was dropwise added during 20 minutes. The reaction mixture was then refluxed for 4 hours. Excess of acetone was evaporated. The residue was dissolved in 100 ml cold water, charcoaled and filtered. Acidification gave 10 g (near theory) of white crystalline powder, MP 118°–120°.

2-(4-carboxamidophenoxy)-2-methylpropionic acid 2-(4-cyanophenoxy)-2-methylpropionic acid 11.3 g (0.055 mole) was added to a solution of 280 ml 3% hydrogen peroxide and 8 g KOH in 32 ml H$_2$O in a 1 lit. flask. The mixture was stirred until gas evaluation and exothermic reaction was terminated. After cooling, the reaction mixture was acidified (HCl) to give 10.8 g (88%) of a white crystalline compound, MP 202°–204°.

2-(4-Aminophenoxy)-2-methylpropionic acid 2-(4-carboxaminophenoxy)-2-methylpropionic acid, 11.15 g (0.05 mole) were gradually added to a cold stirring solution of 3 ml bromine which were added to an ice cold solution of 12 g NaOH in 100 ml water. Stirring continued for 5 minutes to dissolve the amide. The solution was then warmed to about 75° for 20 minutes. The colored solution was cooled and acidified with acetic acid giving 8.84 (90%) of colorless small crystals, MP 214°–216°. This compound is reacted with 3,5-dichlorophenyl isocyanate to form 2(4(3,5-dichlorophenylureido)phenoxy)2-methylpropionic acid.

EXAMPLE 2

4-ethoxycarbonylaminophenol

This already reported compound (Beilstein Der Organischen Chemie 13 478 (1930), was prepared by the following method:

p-aminophenol 33.36 g (0.3 mole) and 12 g NaOH were dissolved in 120 ml water and cooled to ice salt bath temperature. To the stirring solution, 24 ml ethylchloroformate were slowly added. A white precipitate was found. One gram sodium dithionite was added and mixed. The solid was filtered by suction and washed with cold water (50 ml). Recrystallization from hot water gave a crystalline powder, 48.3 g (89%), MP 120°–123°.

2-(4-aminophenoxy)2-methylpropionic acid 4-ethoxycarbonylaminophenol 6.335 g (0.035 mole) and 7.5 g NaOH were added to 30 ml acetone. To the refluxing mixture 2.5 ml chloroform were dropwise added. While the mixture was stirring, it was refluxed for four hours. Excess of the solvent was evaporated. The residue was dissolved in water and acidified. A light brown oil was obtained which slowly turned to a crystalline mass 4.5 g (48%) mP 82°–83°. The above ester was boiled with 45 ml 10% KOH in water for half hour. After cooling, the reaction mixture was acidified with concentrated acetic acid to give 2.86 g (87%) of desired compound. This compound may be reacted with the isocyanate as in Example 1 to form the same product of Example 1.

EXAMPLE 3

2-(4-aminophenoxy)-2-methylpropionic acid

To a refluxing mixture of 4-ethoxycarbonylaminophenol 12.67 g (0.07 mole) and 15 g NaOH in 60 ml acetone, 5 ml chloroform were dropwise added. Stirring and refluxing continued for 4 hours. At the end, excess of acetone was evaporated. A solution of 20 g KOH in 75 ml water was added and boiled for half hour. After cooling, the solution was acidified with acetic acid to give 2-(4-aminophenoxy)-2-methylpropionic acid as a white crystalline compound, 7.15 g (51%), MP 216°–218°.

2-(4-(3,5-dichlorobenzamido)phenoxy)-2-methylpropionic acid

To a solution of 0.5 g 2-(4-aminophenoxy)-2-methylpropionic acid in 5 ml 2N NaOH, 0.70 ml 3,5-dichlorobenzoyl chloride was dropwise added with stirring 5 ml additional 2N NaOH was gradually added to keep the PH strongly alkaline during the reaction. After 1 hour stirring, the reaction product was acidified with HCl. The white precipitate was recrystallized from aqueous isopropanol to give 1.4 g (76%) of fine crystals MP 206°–207°.

EXAMPLE 4

2-(4-(3,5-Dichlorophenylureido)phenoxy)-2-methylpropionic acid

To a stirring solution of 4.95 g (0.025 mole) of 2-(4-aminophenoxy)-2-methylpropionic acid in 50 ml dry pyridine, 4.95 g (0.025 mole) of 3,5-dichlorophenyl isocyanate were added. After 1 hour stirring at room temperature, 150 ml water was added and the mixture was acidified with concentrated HCl. The precipitate was filtered, washed several times with cold water and dried. Recrystallization from aqueous acetone gave small plates 1.81 g (94%) MP 182°–184°.

EXAMPLE 5

2-(4-(2,4,5-trichlorophenylureido)phenoxy)-2-methylpropionic acid

This compound was prepared in pyridine as described in Example 4. Yield 96% MP 216°–216°.

EXAMPLE 6

2-(4-(3,4,5-trichlorophenylureido)phenoxy)-2-methyl propionic acid

This compound was prepared in pyridine as described in Example 4. Yield 90% MP 233°–235°.

The structure of all compounds prepared were confirmed by spectroscopical and analytical methods.

EXAMPLE 7

2-(4-(3,4-dichlorophenylureido)phenoxy)-2-methylpropionic acid

To a stirring solution of 1.09 g (0.01 mole) P-aminophenol in 10 ml pyridine, 1.88 g (0.01 mole) 3,4-dichlorophenylisocyanate were added. The reaction was exothermic. After 20 minutes, stirring at room temperature, 50 ml water were added and pyridine was neutralized by dropwise addition of 5% Hcl. The white crystalline powder was filtered, washed with water and dried giving 2.95 g (99%) of desired compound, MP 208°–210°. A mixture of the 1-(3,4-dichlorophenyl)-3-(4-hydroxyphenyl)urea 2.5 g, NaOH 1.79 g in 12.5 ml acetone was stirred and heated to reflux. To the mixture, 0.85 ml chloroform was dropwise added. After 4 hours refluxing, most of acetone was evaporated. The residue was dissolved in 50 ml hot water, charcoaled and filtered. It was then acidified with HCl. The compound was recrystallized in 20% acetic acid or aqueous acetone to give 2.6 g (81.5%), MP 183°–184°.

EXAMPLE 8

2-(4-(3,5-difluorophenylureido)phenoxy)-2-methylpropionic acid

This compound was prepared in pyridine according to the general method of Example 4. Yield 92%. MP 181°–183°.

The compounds synthesized according to the procedures described in this patent application were tested for their abilities to modify the affinity of hemoglobin for oxygen. The test procedures employed included determination of the standard oxygen dissociation curve by Hemox Analyzer (ICS Med. Products, Huntington Valley, Penna). In this test, P50 represents the partial pressure of $O_2$ (in mmHg) at which 50% of the oxygenated 2 Compounds which hemoglobin is converted to hemoglobin. reduce affinity of hemoglobin for oxygen shift the dissociation curve to the right and increase the P50 values. The results of these tests are given in Table 1 comprising activities of various compounds at various concentrations tested against a solution of purified hemoglobin or a standard suspension of human red blood cells in HEPES buffer at pH 7.4.

TABLE 1

| Compound | Concentration (mM) | P50% Hemoglobin | P50% Red Blood Cells |
|---|---|---|---|
| 1 | 0 | 8.25 ± 2 | 12 ± 1.68 |
| 2 | 1.0 | — | 16 ± 1.32 |
|   | 0.2 | 8.5 | — |
| 3 | 1.0 | — | 64 |
|   | 0.2 | — | 25.5 |
| 4 | 1.0 | — | 35.5 |
|   | 0.5 | — | 33 |
|   | 0.2 | 10 | 22.5 |
| 5 | 0.2 | 12 | 15 |
| 6 | 0.5 | 45 | 57.5 |
|   | 0.2 | 20.5 | 26 |
| 7 | 1.0 | — | 18 |
|   | — | — | 14 |
| 8 | 0.2 | 61 | — |
|   | 0.1 | 21 | — |
| 9 | 0.2 | 64 | — |
|   | 0.1 | 25 | — |

1. Control - HEPES buffer at pH 7.4
2. Bezafibrate
3. 2-(4-(3,4-dichlorophenylureido)phenoxy)-2-methylpropionic acid
4. 2-(4-(2,4-dichlorophenylureido)phenoxy)-2-methylpropionic acid
5. 2-(4-(2,5-dichlorophenylureido)phenoxy)-2-methylpropionic acid
6. 2-(4-(3,5-dichlorophenylureido)phenoxy)-2-methylpropionic acid
7. 2-(4-(3,5-difluorophenylureido)phenoxy)-2-methylpropionic acid
8. 2-(4-(2,4,5,-trichlorophenylureido)phenoxy)-2-methylpropionic acid
9. 2-(4-(3,4,5-trichlorophenylureido)phenoxy)-2-methylpropionic acid A dash indicates that no test was carried out.

The exceptionally high activities of compounds 6, 8 and 9 are documented in Table 1 not only by their higher P50 values as compared to bezafibrate and compound 3, but also by the observation that for all compounds except for compounds 6, 8 and 9, the activity rapidly falls off or is lost when the concentration is reduced to 0.1 mM.

Compounds 8 and 9 show exceptional in vitro activity even at 0.1 mM concentration..

The commercial compound bezafibrate has no activity in this test at levels below 0.5 mM.

I claim:

1. A compound of the formula:

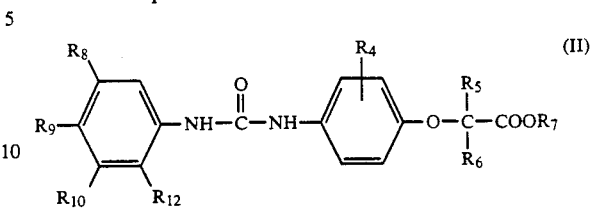

wherein $R_4$ is selected from the group consisting of hydrogen, halogen, straight and branched chain alkyl of from 1 to 6 carbon atoms, aryl, cycloakyl of 3 to 7 carbon atoms; and alkoxy of 1 to 6 carbon atoms; $R_5$ and $R_6$ may be the same or different and are selected from the group consisting of hydrogen, halogen, straight and branched chain alkyl groups of from 1 to 6 carbon atoms; aralkyl groups wherein the alkyl portion has from 1 to 6 carbon atoms, cycloalkyl of from 3 to 7 carbon atoms and aryl; $R_7$ is hydrogen or a straight or a branched chain alkyl group of 1 to 6 carbon atoms; $R_8$ is halogen; $R_9$ is halogen or hydrogen with the proviso that $R_9$ may only be hydrogen when $R_8$ and $R_{12}$ are halogen; $R_{10}$ is halogen or hydrogen and $R_{12}$ is halogen or hydrogen and the pharamaceutically acceptable salts thereof.

2. A compound as defined in claim 1, wherein $R_4$ is hydrogen, $R_5$ and $R_6$ are methyl, $R_7$ is hydrogen, $R_8$ is chloro, $R_9$ is chloro, $R_{10}$ is chloro and $R_{12}$ is hydrogen.

3. A compound as defined in claim 1, wherein $R_4$ is hydrogen, $R_5$ and $R_6$ are methyl, $R_7$ is hydrogen, $R_8$ is chloro, $R_9$ is hydrogen, $R_{10}$ is chloro and $R_{12}$ is chloro.

4. A compound as defined in claim 1, wherein $R_{12}$ is chloro, $R_{10}$ is hydrogen, $R_9$ is chloro, $R_8$ is chloro, and $R_4$, $R_5$, $R_6$ and $R_7$ are hydrogen.

5. a pharmaceutical composition, which comprises a compound as defined in claim 1 and a pharmaceutically acceptable diluent.

6. A pharmaceutical composition, which comprises a compound of claim 2 and a pharmaceutically acceptable diluent.

7. A pharmaceutical composition which comprises a compound of claim 3 and a pharmaceutically acceptable diluent.

8. A pharmaceutical composition, which comprises a compound of claim 4 and a pharmaceutically acceptable carrier.